United States Patent

Sabee et al.

[11] 4,013,816
[45] Mar. 22, 1977

[54] STRETCHABLE SPUN-BONDED POLYOLEFIN WEB

[75] Inventors: Reinhardt N. Sabee; C. Craig Sabee, both of Appleton, Wis.

[73] Assignee: Draper Products, Inc., Appleton, Wis.

[22] Filed: Nov. 20, 1975

[21] Appl. No.: 633,991

[52] U.S. Cl. .............................. 428/288; 128/284; 156/167; 264/DIG. 75; 264/210 F; 428/198; 428/296; 428/364

[51] Int. Cl.² .......................................... D04H 3/14

[58] Field of Search ............... 264/DIG. 75, 210 F; 156/167, 178; 428/288, 296, 364; 128/155, 284, 290 R, 296

[56] References Cited

UNITED STATES PATENTS

| | | | |
|---|---|---|---|
| 3,441,468 | 4/1969 | Siggel et al. | 264/DIG. 75 |
| 3,502,763 | 3/1970 | Hartmann | 264/210 F |
| 3,509,009 | 4/1970 | Hartmann | 428/296 |
| 3,554,854 | 1/1971 | Hartmann | 264/DIG. 75 |
| 3,615,998 | 10/1971 | Kolb | 264/DIG. 75 |
| 3,806,289 | 4/1974 | Schwartz | 264/115 |
| 3,825,380 | 7/1974 | Harding et al. | 264/DIG. 75 |
| 3,849,241 | 11/1974 | Butin et al. | 264/210 F |
| 3,918,995 | 11/1975 | Palmer et al. | 264/DIG. 75 |

*Primary Examiner*—James J. Bell
*Attorney, Agent, or Firm*—Wheeler, Morsell, House & Fuller

[57] ABSTRACT

This invention relates to a stretchable spun-bonded web suitable as top-liner for a disposable diaper, pad, bandage and the like, and a process for making the same. In particular, the invention relates to a polyolefin web where the crossover points of the fibers do not rupture when the web is stretched to 50% of its original length, but maintains approximately its original structure, which makes it extremely suitable for such applications. The web is made by melt blowing polypropylene of less than 1.2 intrinsic viscosity at a filament velocity of at least 15 meters per second on a smooth collecting surface having a temperature less than 65° F.

4 Claims, 7 Drawing Figures

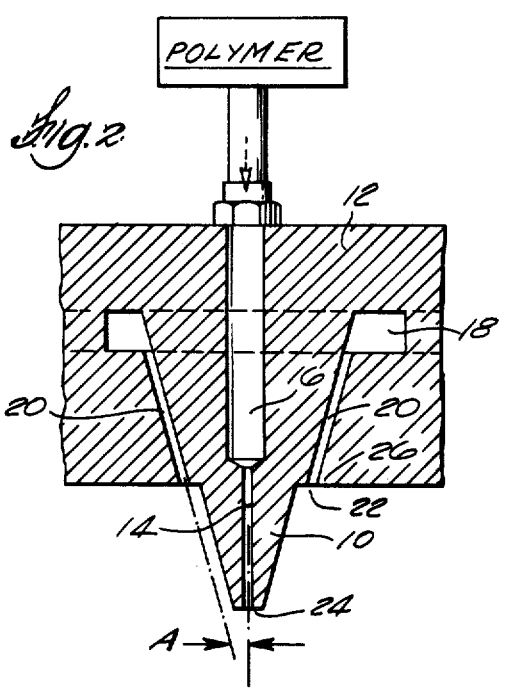
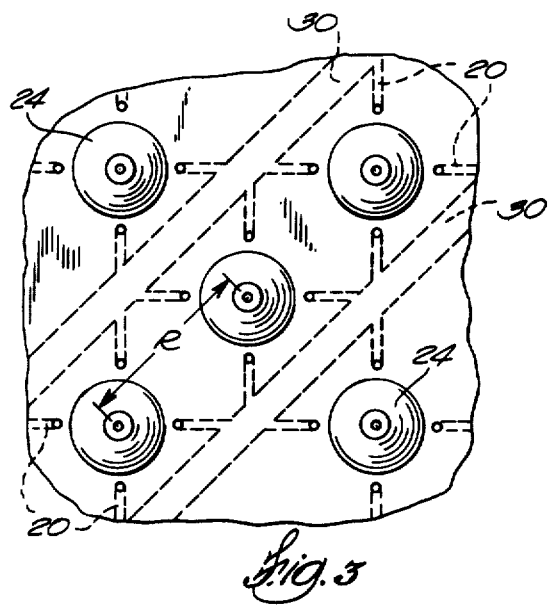
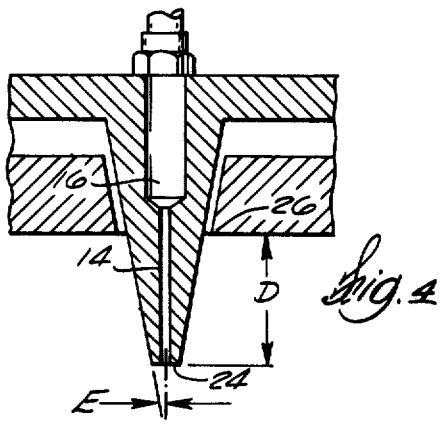
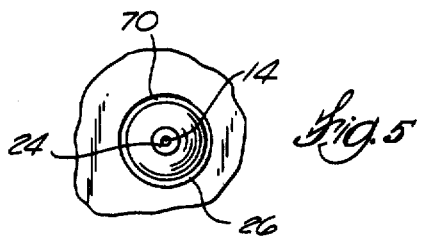
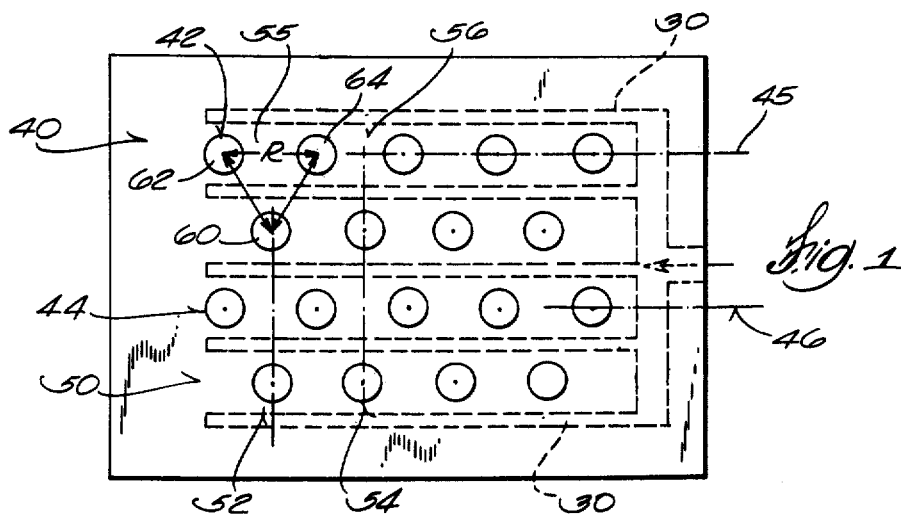

4,013,816

STRETCHABLE SPUN-BONDED POLYOLEFIN WEB

BACKGROUND OF INVENTION

The most severe deficiency of composite pad products is the splitting of the web upon minor amounts of strain, which causes the underlying layers of absorbed material to disintegrate and fall out of the diaper or pad structure, which can cause irritation of the skin and other discomfort. A stretchable web overcomes these problems.

Several spun-bonded processes, especially those using a "melt-blowing" concept, are known in the prior art such as Hartmann, U.S. Pat. No. 3,502,763 and Butin, U.S. Pat. No. 3,849,241, which show the production of melt-blown webs of fine enough filament size, but the webs are lacking in one or more of the essential and critical properties, like bond strength of the filament crossover points or yield to stress (splittiness). In the present invention, these deficiencies are overcome by a unique combination of process parameters and material properties that achieves the desired balance of the required web properties which make it suitable as top liner for diapers, pads, and the like.

Stretchability is generally achieved by low molecular orientation of a filament as e.g., measured by its birefringence. Low birefringence is usually accompanied with relatively slow spinning speeds (see Hartmann, U.S. Pat. No. 3,502,763). At high spinning speeds, usually high birefringence and strength, accompanied with low residual elongation of the filaments is obtained, which in many applications is preferred. To obtain economically practical spinning rates as well as the desired low molecular orientation, it is necessary to spin at extremely low melt-viscosity requiring high temperatures and using very low molecular weight polymers. High spinning rates and filament velocities are furthermore required in order to form strong bonds of filament crossover points caused by impact of the filaments on the collecting surface, where the filaments are still tacky when the web is formed. This method, however, produces a web of low birefringence but high crystallinity; the high crystallinity in turn causes brittleness in low molecular weight fibers such as used in this process, which causes the undesirable splittiness.

SUMMARY OF INVENTION

The invention provides a spun-bonded web in which the crossover points of the fibers do not rupture when stretched up to 50% of the original web length and thus, is suitable as a liner for various composite pads such as diapers or bandages. The web is formed by melt blowing polypropylene having an intrinsic viscosity of less than 1.2 and with filament velocity exceeding a certain minimum and at least 15 meters per second. The collecting surface of the web is smooth and maintained at temperature of less than 65° F. Splittiness is avoided by rapid cooling which keeps the filaments amorphous.

The cooling rates required for the spun-bonded web described herein are extremely fast and have not been described in the prior art. It has been found that effective cooling to obtain stretchability as well as strong bonding of crossover points is a factor influenced by a combination of filament velocity at impact on the collecting surface, temperature of the collecting surface, filament size and web basis weight.

Further objects, advantages and features of the invention will become apparent from the following disclosure.

DESCRIPTION OF DRAWINGS

FIG. 1 is a diagrammatic plan view of a spinnerette head showing an extrusion nozzle pattern which can be employed for practicing the invention.

FIG. 2 is an enlarged sectional view of one type of extrusion nozzle.

FIG. 3 is a fragmentary bottom view of a spinnerette head employing the nozzles shown in FIG. 2.

FIG. 4 is an enlarged sectional view of a modified form of an extrusion nozzle which can be used to practice the invention.

FIG. 5 is a plan view of the nozzle shown in FIG. 4.

DESCRIPTION OF PREFERRED EMBODIMENT

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

The FIGS. 1 through 5 show two embodiments of extrusion nozzles as disclosed in our prior application Ser. No. 573,237 now abandoned. The invention set forth herein does not require use of the precise geometry and pattern of these nozzles, and other extrusion nozzles can be employed to practice the invention. However, the examples presently set forth were based on use of such nozzles and will be described herein as illustrative of the type of nozzle which can be employed.

Figure 6:
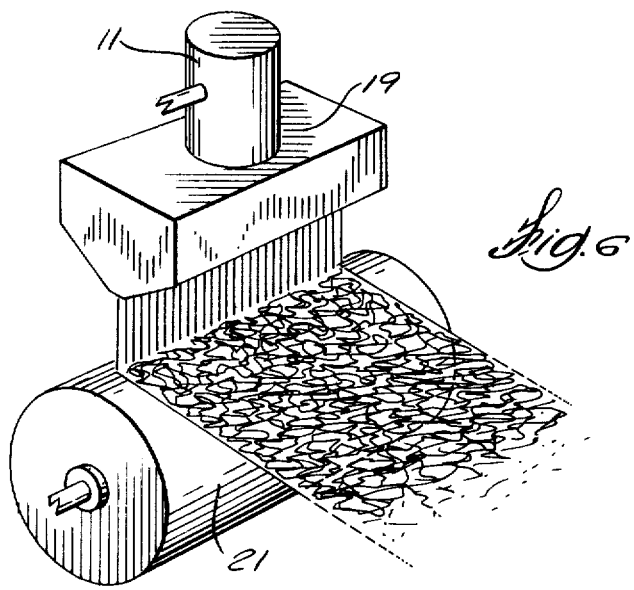
FIG. 6 is a diagrammatic view of extrusion apparatus and the collecting surface.

The nozzle 10 in FIG. 2 is part of a spinnerette plate 12 connected to an extruder 19 shown in FIG. 6. A fiber forming thermoplastic polymer is set into the capillary 14 at a specified rate. Compressed hot air is fed into the manifold 18 and blown out the air capillaries 20. The filaments are collected on cooled, smooth-surfaced drum 21 (FIG. 6). The angle A in FIG. 2 and distance D, FIG. 4 are important aspects of the invention disclosed in the prior application Ser. No. 573,237.

In the examples subsequently described, the important parameters of the invention are determined.

EXAMPLE 1

Polypropylene of Melt Flow Rate 35 (ASTM Method 1232-62T) and an intrinsic viscosity of 1.6 was fed to a 1 inch extruder 19 having a 24/1 length/diameter screw design.

The resin was extruded at a rate of 27 gram/min. through a die having 18 nozzles in a pattern arrangement as shown in FIG. 1. The nozzle pattern shown in FIG. 1 includes first and second superposed arrays 40, 50 of nozzles. The first array 40 includes nozzle rows 42, 44 with the nozzles spaced equally a distance R along axes 45, 46. The second array 50 includes nozzle rows 52, 54 with the nozzles spaced equally along the row axes 55, 56 a distance greater than R. The axes 55, 56 intersect the axes 45, 46 at the midpoint or ½ R along the rows 40, 44. The distance between nozzle 60 and nozzles 62, 64 is equal to R.

In Example 1 the die temperature was 700° F. The cone-shaped nozzles, having a cone angle of E (FIG. 4) of 40°, were separated from each other (R) by 0.25 inch and distance D was ⅜ inch long. The extrusion capillary 14 inside the cone had a length of ⅜ inch and a diameter of 0.025 inch. Each nozzle had at the base of the cone three air orifices 20 of 0.019 inch diameter, at 120° separation, pointing at an angle A of 20° and parallel to the cone surface, to the tip 24 of the nozzle. The temperature zones of the extruder were varied to result in different amounts of degradation and melt viscosities at the extrusion nozzles. By adjusting the air pressure in the nozzles, the denier per filament of each run was held approximately constant at 3 dpf. Table 1 shows the data of the webs collected 12" from the nozzles on a rotating chilled drum 21 of 50° F. It can be seen from Table 1, that the birefringence of the filaments, increases with increasing viscosity of the web filaments while the web tensile elongation decreases.

minimum web tensile elongation of 50%. This example demonstrates that in addition to these variables, a combination of filament size (dpf) and basis weight is required to obtain stretchability. The data are listed in Table 3 and plotted in FIG. 7.

Figure 7:
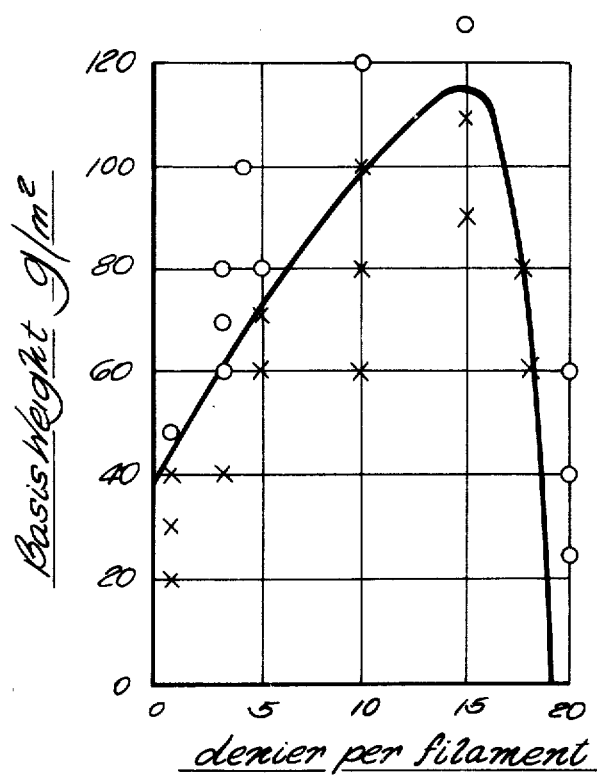
FIG. 7 is a graph showing web elongation and correlated with basis weight and denier per filament.

The web having usable properties are all within the curve A of FIG. 7 (minimum of 50% web tensile elongation). The line A can be described by the simple formula:

$$\text{Basis weight (g/m}^2\text{)} = 7\,dpf + \frac{200}{dpf - 20} + 50$$

It is recognized that the effect and rate of cooling in a web formed on impact on a cold smooth surface is influenced by both filament size (Dpf) and basis weight, and the mechanism of heat transfer is very complex.

Accordingly to FIG. 7, the maximum basis weight is

TABLE 1

| Run No. | | 1 | 2 | 3 | 4 | 5 | 6 | 7 |
|---|---|---|---|---|---|---|---|---|
| Extruder Zone | 1 °F | 400 | 400 | 400 | 400 | 400 | 400 | 400 |
| | 2 | 500 | 500 | 500 | 550 | 550 | 550 | 550 |
| | 3 | 550 | 550 | 550 | 600 | 600 | 600 | 600 |
| | 4 | 600 | 650 | 700 | 650 | 700 | 750 | 800 |
| intrinsic viscosity web | | 1.4 | 1.3 | 1.1 | 1.0 | 0.8 | 0.6 | 0.5 |
| birefringence (filaments) | | 0.020 | 0.015 | 0.012 | 0.010 | 0.006 | 0.004 | 0.002 |
| dpf | | 3.1 | 3.0 | 3.2 | 3.2 | 2.0 | 2.8 | 2.9 |
| filament velocity m/sec | | 72 | 75 | 70 | 70 | 80 | 80 | 77 |
| air (psi) | | 25 | 18 | 13 | 10 | 7 | 5 | 4 |
| web tensile elongation, % at break | | 40 | 45 | 50 | 60 | 150 | 80 | 75 |
| web basis weight gram/meter² | | 25 | 26 | 25 | 25 | 26 | 27 | 26 |

EXAMPLE 2

Filament velocity at about 3 dpf was varied in the same melt-blowing die by varying polymer through-put per nozzle and air pressure. Although the birefringence was very low at the slower speeds, bonding of filament crossover points became less efficient below 15 m/sec, as seen under a microscope after stretching a 1 inch strip of web to 50% elongation.

116 g/m² at 16 dpf, and the maximum allowable dpf is about 20, above which cooling is apparently too slow even in a single filament to eliminate brittleness of the web.

The denier per filament of the webs shown in Table 3 and FIG. 7 were adjusted by changing the throughput per nozzle and air pressure in the spinning die, and the basis weight of the web was adjusted by changing the speed of the cylindrical collecting drum 21. The drum,

TABLE 2

| Extruder zones: as in Example 1, Run 5 | | | Run | | |
|---|---|---|---|---|---|
| | 1 | 2 | 3 | 4 | 5 |
| intrinsic viscosity | 0.8 | 0.8 | 0.7 | 0.7 | 0.7 |
| dpf | 3.1 | 2.9 | 2.9 | 2.8 | 2.8 |
| throughput/nozzle Gram/min | 1.65 | 1.20 | 0.68 | 0.37 | 0.28 |
| filament velocity m/sec | 80 | 62 | 35 | 20 | 15 |
| birefringence | 0.007 | 0.005 | 0.003 | 0.002 | 0.001 |
| % crossover points broken at 50% elongation | 0 | 0 | 10 | 10 | 50 |

EXAMPLE 3

In the previous examples it was shown that the filament velocity has to exceed a certain minimum, and the birefringence be below a certain maximum, in order to obtain a web of good bond strength and a had a smooth metal surface and a surface temperature of 45° F.

Web elongation at break determination:

Elongation at break was determined in a tensile tester, using a web strip of one-half inch, width, clamp distance 2 inches, and a draw rate of 10 inch/minute.

TABLE 3

| Melt-blown webs of varying dpf and basis weight: Throughput per nozzle (g/min) | air pressure (psi) | dpf | basis weight (g/m²) | % web strip elongation at break |
|---|---|---|---|---|
| 0.3 | 6 | 1 | 20 | 125 |
|  |  |  | 30 | 85 |
|  |  |  | 40 | 51 |
|  |  |  | 45 | 42 |
| 1.1 | 10 | 3 | 40 | 75 |
|  |  |  | 60 | 49 |
|  |  |  | 70 | 34 |
|  |  |  | 80 | 31 |
| 1.2 | 12 | 5 | 60 | 68 |
|  |  |  | 70 | 52 |
|  |  |  | 80 | 38 |
|  |  |  | 100 | 29 |
| 3.1 | 12 | 10 | 60 | 74 |
|  |  |  | 80 | 62 |
|  |  |  | 100 | 52 |
|  |  |  | 120 | 39 |
| 4.5 | 10 | 15 | 90 | 62 |
|  |  |  | 110 | 53 |
|  |  |  | 130 | 35 |
| 4.5 | 8.1 | 18 | 60 | 58 |
|  |  |  | 80 | 50 |
|  |  |  | 100 | 41 |
| 4.5 | 7 | 20 | 25 | 48 |
|  |  |  | 40 | 42 |
|  |  |  | 60 | 30 |
|  |  |  | 100 | 28 |

EXAMPLE 4

This example demonstrates the importance of the surface temperature of the collecting surface: a 30 g/m² web of about 3 dpf filament size was formed under extrusion conditions of Table 1, run 5. Table 4 shows web elongation at break versus drum temperature, indicating that at a temperature above 60° F the web does no longer have the desired stretchability.

(the relation of dpf and filament diameter for round polypropylene is: diameter (in micron) = 12.5 $\sqrt{dpf}$)

TABLE 4

| drum surface temperature ° F | % web tensile elongation at break |
|---|---|
| 40 | 120 |
| 45 | 95 |
| 50 | 74 |
| 55 | 61 |
| 60 | 43 |
| 65 | 35 |

FIG. 7 is a curve based on the data set forth in Table 3 which shows the percent web strip elongation at break for webs of differing basis weight and denier per filament. Only a web which falls on the curve or within the curve has the desired web elongation at break of larger than 50%.

In FIG. 7 the X indicates a web having an elongation at break greater than 50% and the O indicates a web having an elongation at break of less than 50%.

We claim:

1. A spun-bonded polypropylene web having at least 50% tensile web elongation at break, a filament size of 20 dpf or less, a basis weight in gram/square meter which is lower than the sum of:

$$7\,dpf + \frac{200}{dpf - 20} + 50$$

where dpf refers to the filament of the corresponding web, said filaments having a birefringence of less than 0.0120 and wherein more than 70% of all filament cross-over points are fuse bonded and wherein said fused bonds do not separate when the web is stretched to 50% of its original dimension.

2. A web in accordance with claim 1 formed by melt-blowing polypropylene of less than 1.2 intrinsic viscosity at a filament velocity of at least 15 m/sec onto a collector having a chilled smooth surface maintained at a temperature of less than 65° F.

3. A web in accordance with claim 2 wherein said smooth surface is the periphery of a drum.

4. A spun-bonded polypropylene web having at least 50% tensile web elongation at break, the filaments of said web being extruded at a velocity in excess of 15 meters per second onto a chilled surface having a temperature less than 65° and having a size of 20 denier per filament dpf or less, a basis weight in grams/square meter which is less than the sum of 7 times denier per filament plus 200 divided by denier per filament minus 20 and plus 50, said filaments having a birefringence of less than 0.0120 and wherein more than 70% of all filament crossover points are fuse bonded and wherein said fused bonds do not separate when the web is stretched to 50% of its original dimension.

* * * * *